United States Patent [19]

Klayman et al.

[11] Patent Number: 4,665,173

[45] Date of Patent: May 12, 1987

[54] 2-ACETYL- AND 2-PROPIONYLPYRIDINE SELENOSEMICARBAZONES

[76] Inventors: Daniel L. Klayman, 8025 Ellingson Dr., Chevy Chase, Md. 20815; John P. Scovill, 1501 Crest Rd., Silver Spring, Md. 20902

[21] Appl. No.: 364,085

[22] Filed: Mar. 31, 1982

[51] Int. Cl.[4] .................. C07D 401/12; C07D 413/12
[52] U.S. Cl. .................................... 540/597; 540/583; 544/131; 544/238; 544/360; 544/364; 546/16; 546/104; 546/145; 546/163; 546/171; 546/193; 546/264; 546/273; 546/275; 546/283; 546/284; 546/285; 546/281; 546/332
[58] Field of Search ............... 544/131, 360, 238, 364; 546/332, 264, 284, 283, 273, 104, 163, 171, 285, 275, 281, 193, 145, 16; 260/244.4; 540/583, 597

[56] References Cited

PUBLICATIONS

Klayman et al, *Chemical Abstracts,* vol. 95, No. 168944w; Chemical Substance Index, p. 3463CS (1981).
Dobek et al, *Chemical Abstracts,* vol. 93, No. 161813c; Chemical Substance Index, p. 3180CS (1980).
Bilinski et al, *Chemical Abstracts,* vol. 84, No. 30970t; Chemical Substance Index, p. 2507CS (1976).
Dobek et al, *Antimicrobial Agents and Chemotherapy,* vol. 18, Jul. 1980, pp. 27–36.

*Primary Examiner*—Robert W. Ramsuer
*Attorney, Agent, or Firm*—William G. Gapcynski; Arthur I. Spechler; Werten F. W. Bellamy

[57] ABSTRACT

This invention relates to novel 2-acetyl- and 2-propionylpyridine selenosemicarbazones. These compounds are useful as antimalarial and antileukemic agents. Also disclosed are several synthetic procedures used to prepare the selenosemicarbazones.

9 Claims, No Drawings

2-ACETYL- AND 2-PROPIONYLPYRIDINE SELENOSEMICARBAZONES

GOVERNMENT INTEREST

The invention described herein may be manufactured, licensed and used by or for the Government, for governmental purposes, without the payment of any royalties to us thereon.

BACKGROUND OF THE INVENTION

Applicants reported in the *Journal of Medicinal Chemistry,* 1979, Vol. 22 at pages 855 and 1367 on a series of thiosemicarbazones derived from 2-acetylpyridine which possess significant antimalarial activity. The molecular features which have been shown to be essential for antimalarial activity are the presence of a 2-pyridylalkylidene moiety, an attached thiocarbonyl or selenocarbonyl group (in contrast to a carbonyl group) as reported in *Eur. J. Med. Chem.,* 1981, Vol. 16, page 317, and the presence of certain bulky substituents at position $N^4$.

In view of the electronic similarity of selenium to sulfur, applicants decided to test selenium analogs of two of the more active antimalarial compounds, namely, N-[4-(2-pyridyl)piperazine]-2-[1-(2-pyridyl)ethylidene]hydrazinecarbothioamide (compound 1) and N-(2-,6-dimethylmorpholine)-2-[-(2-pyridyl)ethylidene]hydrazinecarbothioamide (compound 2). Whereas

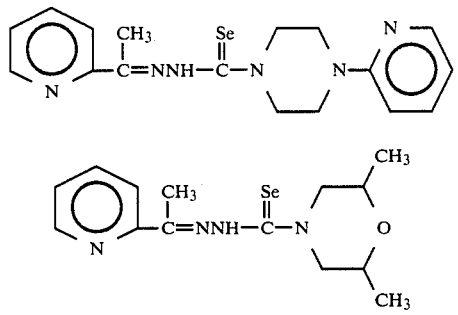

compound 1 had diminished antimalarial activity relative to its sulfur analog, compound 2 had antimalarial activity comparable to its sulfur analog with surprisingly lower toxicity.

In view of these considerations, applicants decided to prepare 2-acetyl- and 2-propionylpyridine selenosemicarbazones in order to investigate their antimalarial and antileukemic properties.

DETAILED DESCRIPTION OF THE INVENTION

This invention relates to novel selenosemicarbazone compounds and their pharmaceutically-acceptable acid addition salts depictable by the following formula which are useful in the treatment of malaria and leukemia:

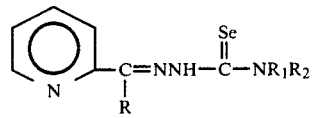

or a pharmaceutically-acceptable acid addition salt wherein R is methyl or ethyl; $R_1$ is hydrogen, alkyl, preferably having 1 to 12 caarbon atoms or more, preferably 6 to 12 carbon atoms; cycloalkyl, preferably having 3 to 10 carbon atoms; substituted alkyl wherein the alkyl group preferably has 1 to 12 carbon atoms and the substituent group is amine, alkylamino (preferably 1 to 4 carbon atoms), dialkylamino (preferably 1 to 4 carbon atoms in each alkyl group), cycloalkyl (preferably 3 to 10 carbon atoms), hydroxy, C(O)Oalkyl (preferably 1 to 4 carbon atoms in the alkyl group), phenyl, or pyridyl; alkenyl, preferably having 2 to 6 carbon atoms; alkynyl, preferably having 3 to 6 carbon atoms; substituted benzyl wherein the substituent is methyl or phenyl on the alpha carbon atom, or the substituent is alkyl (preferably methyl), dialkyl (preferably dimethyl), halo, dihalo, or alkoxy (preferably ethoxy) on the phenyl ring; adamantyl; phenyl, naphthyl; substituted phenyl or substituted naphthyl wherein the ring is mono-, di-, or trisubstituted and the substituents are alkyl (preferably 1 to 4 carbon atoms), halo (preferably fluoro), alkoxy (preferably 1 to 4 carbon atoms), hydroxy, phenoxy, trifluoromethyl, dialkyl (preferably dimethyl) amino, dialkylaminoalkyl (preferably diethylaminomethyl), or C(O)Oalkyl (preferably 1 to 4 carbon atoms in the alkyl group); pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:

(1) alkylenimino;

(2) alkylenimino which may contain one double bond and/or is mono- or disubstituted with alkyl (preferably 1 to 4 carbon atoms), hydroxy, phenyl, or benzyl;

(3) alkylenimino which is either bridged by an alkylene group (preferably 2 carbon atoms) or is fused to a phenyl ring; or is attached by a spiro linkage to an ethylene ketal group;

(4) homopiperazinyl; homopiperazinyl substituted with alkyl (preferably 1 to 4 carbon atoms); piperazinyl; or piperazinyl substituted with alkyl (preferably 1 to 4 carbon atoms), dialkyl (preferably 1 to 4 carbon atoms in each alkyl group), phenyl, C(O)Oalkyl (preferably 1 to 4 carbon atoms in the alkyl group), trifluoromethylphenyl, halophenyl, benzyl, or pyridyl; and (5) morpholino, dialkyl (preferably 1 to 4 carbon atoms in each alkyl group) morpholino.

When $R_1$ and $R_2$ are taken together with the nitrogen atom to which they are attached, the resulting heterocyclic ring is preferably one of the following: azetidino; pyrrolidino; 2,5-dimethylpyrrolidino; piperidino;

(wherein X is 2-methyl, 3-methyl, 4-methyl, 2-ethyl, 4-hydroxy, 4-phenyl, or 4-benzyl); hexamethylenimino; octamethylenimino; dodecamethylenimino; 2,6-dimethylpiperidino; 3,5-dimethyl piperidino; morpholino; 3,5-dimethylmorpholino;

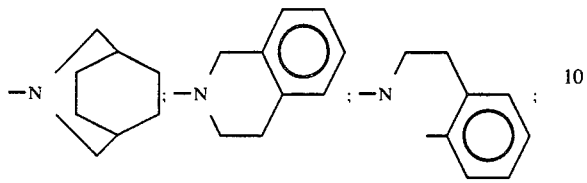

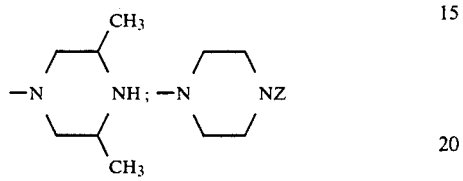

(wherein Z is methyl, phenyl, 3-trifluoromethylphenyl, benzyl, C(O)OEt, 3-pyridyl, 2-pyridyl, or 4-fluorophenyl);

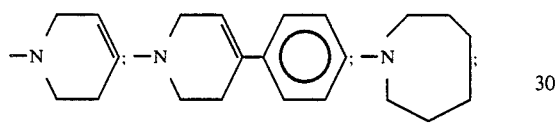

azacyclotridecyl;

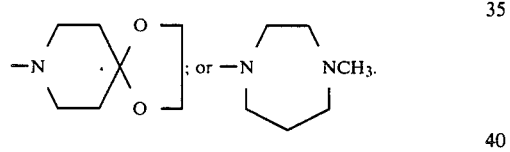

In this disclosure, it is understood that C(O)Oalkyl represents the alkyl carboxylic acid ester; for example, C(O)OEt represents the ethyl carboxylic acid ester.

A partial recitation of specific 2-alkylpyridine selenosemicarbazones contemplated within the scope of applicants' invention is depicted by the following formula:

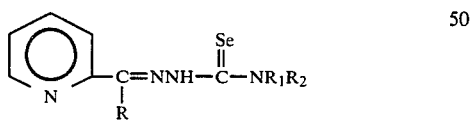

wherein R represents:

1. 

2. 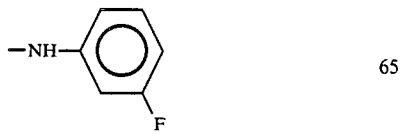

3. 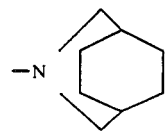

4. —N—CH$_2$(CHOH)$_4$CH$_2$OH

5. —N(CH$_3$)$_2$

6. 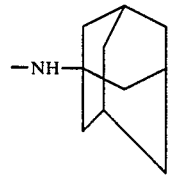

7. 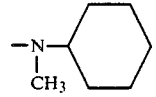

8. —NHCH$_3$

9. —NH$_2$

10. 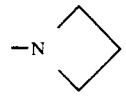

11. 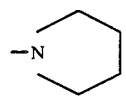

12. 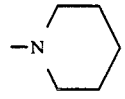

13. 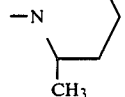

14. 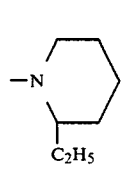

15. 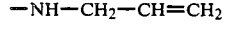

16. —NH—CH$_2$—CH=CH$_2$

17. 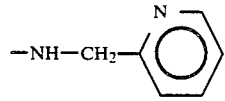

-continued

18. 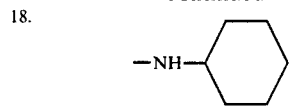

19. 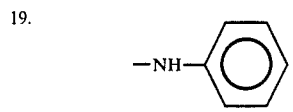

20.  —NHC(CH₃)₂CH₂C(CH₃)₃

21. 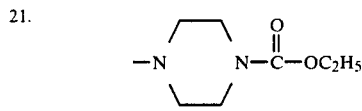

22. 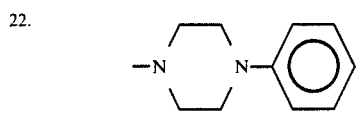

23. 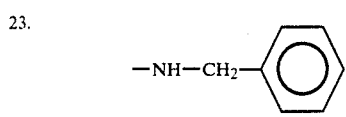

24. 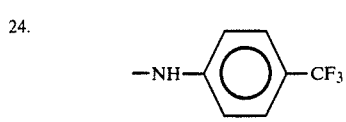

25. 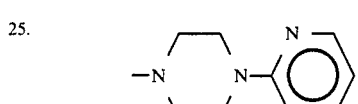

26. 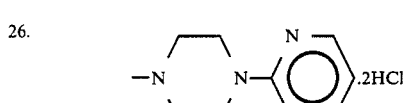 .2HCl

27. 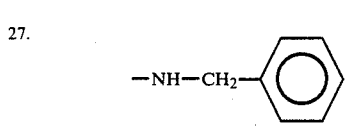

28. 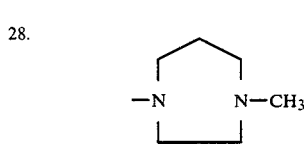

29. —NHCH₂C≡CH

30. —N(C₂H₅)₂

31. —NHCH₂CH₃

32. —NHC₄H₉

33. —NHC₈H₁₇

34. —NHC₁₀H₂₁

35. 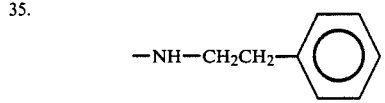

-continued

36. 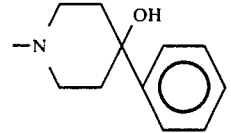

37. 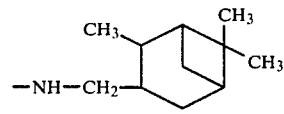

38. 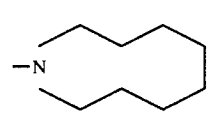

39. 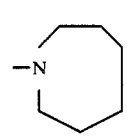

40. 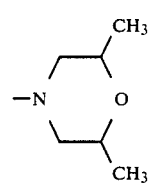

41. 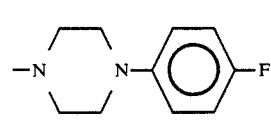

42. 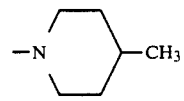

The chemical nomenclature for most of the 2-acetylpyridine selenosemicarbazones depicted in the preceeding paragraph are as follows:

1. 1-Azacycloheptane-1-selenocarboxylic acid 2-[1-(2-pyridyl)ethylidene]hydrazide;
2. 2-Acetylpyridine 4-(3-fluorophenyl)-3-selenosemicarbazone;
3. 3-Azabicyclo[3.2.2]nonane-3-selenocarboxylic acid 2-[1-(2-pyridyl)ethylidene]hydrazide;
4. 1-Methylamino-1-deoxy-D-glucito-N-selenocarboxylic acid 2-[1-(2-pyridyl)ethylidene]hydrazide;
5. 2-Acetylpyridine 4,4-dimethylselenosemicarbazone;
6. 2-Acetylpyridine 4-(1-adamantyl)selenosemicarbazone;
7. 2-Acetylpyridine 4-cyclohexyl-4-methylselenosemicarbazone;
8. 2-Acetylpyridine 4-methylselenosemicarbazone;
9. 2-Acetylpyridine selenosemicarbazone;
10. Azetidine-1-selenocarboxylic acid 2-[1-(2-pyridyl)ethylidene]hydrazide;
11. 1-Azacyclopentane-1-selenocarboxylic acid 2-[1-(2-pyridyl)ethylidene]hydrazide;
12. Piperidine-1-selenocarboxylic acid 2-[1-(2-pyridyl)ethylidene]hydrazide;
13. 2-Methylpiperidine-1-selenocarboxylic acid 2-[1-(2-pyridyl)ethylidene]hydrazide;

14. 2-Ethylpiperidine-1-selenocarboxylic acid 2-[1-(2-pyridyl)ethylidene]hydrazide;
15. 1-Azacyclotridecane-1-selenocarboxylic acid 2-[1-(2-pyridyl)ethylidene]hydrazide;
16. 2-Acetylpyridine 4-allyl-3-selenosemicarbazone;
17. 2-Acetylpyridine 4-(2-picolyl)-3-selenosemicarbazone;
18. 2-Acetylpyridine 4-cyclohexyl-3-selenosemicarbazone;
19. 2-Acetylpyridine 4-phenyl-3-selenosemicarbazone;
20. 2-Acetylpyridine 4-(1,1,3,3-tetramethylbutyl)-3-selenosemicarbazone;
21. 1,4-Diaza-4-carboethoxycyclohexane-1-selenocarboxylic acid 2-[1-(2-pyridyl)ethylidene]hydrazide;
22. 1,4-Diaza-4-phenylcyclohexane-1-selenocarboxylic acid 2[1-(2-pyridyl)ethylidene]hydrazide;
23. 2-Acetylpyridine 4-(2-methylbenzyl)-3selenosemicarbazone;
24. 2-Acetylpyridine 4-(4-trifluoromethylphenyl)-3-selenosemicarbazone and the 3-thiosemicarbazone analog;
25. 1,4-Diaza-4-(2-pyridyl)cyclohexane-1-selenocarboxylic acid 2[1-(2-pyridyl)ethylidene]hydrazide;
26. 1,4-Diaza-4-(2-pyridyl)cyclohexane-1-selenocarboxylic acid 2-[1-(2-pyridyl)ethylidene]hydrazide dihydrochloride;
27. 2-Acetylpyridine 4-benzyl-3-selenosemicarbazone;
28. 1,4-Diaza-4-methylcycloheptane-1-selenocarboxylic acid 2-[1-(2-pyridyl)ethylidene]hydrazide;
29. 2-Acetylpyridine-4-(2-propynyl)-3-selenosemicarbazone;
30. 2-Acetylpyridine-4,4-diethylselenosemicarbazone;
31. 2-Acetylpyridine 4-ethylselenosemicarbazone;
32. 2-Acetylpyridine 4-butylselenosemicarbazone;
33. 2-Acetylpyridine 4-octylselenosemicarbazone;
34. 2-Acetylpyridine 4-decylselenosemicarbazone;
35. 2-Acetylpyridine 4-(2-phenethyl)selenosemicarbazone;
36. (4-Hydroxy-4-phenylpiperidine)-1-selenocarboxylic acid 2-[1-(2-pyridyl)ethylidene]hydrazide;
37. 2Acetylpyridine 4-(3-pinylmethyl)selenosemicarbazone; and
38. 1-Azacyclononane-1-selenocarboxylic acid 2-[1-(2-pyridyl)ethylidene]hydrazide.

The above-described compounds and their pharmaceutically-acceptable acid addition salts are useful in the treatment of malarial infections and leukemia.

With respect to the pharmaceutically-acceptable acid addition salts of this invention, it will be apparent to those of ordinary skill in the art that such salts are contemplated only where the structural features of the compounds permit their preparation. As non-limiting examples of acids used to prepare such salts, hydrochloric and hydrobromic acids are representative.

SYNTHETIC PROCEDURES

Preparation of Thiosemicarbazones

Three synthetic procedures proved to be useful for preparing the thiosemicarbazones of this invention. In Scheme A, a primary amine was converted to the corresponding isothiocyanate (1), ordinarily by employing thiophosgene. Reaction of 1 with hydrazine afforded a thiosemicarbazide 2. Condensation of this intermediate with 2-acetylpyridine provided the 4-monosubstituted thiosemicarbazone 3. However, only thiosemicarbazones monosubstituted at position 4 can be prepared in this manner, as 2-acetylpyridine proved to be usually resistant to condensation with 2,4-disubstituted thiosemicarbazides.

In Scheme A, reaction of hydrazine and carbon disulfide in the presence of sodium hydroxide yielded a carbodithioate. Alkylation of this carbodithioate with either iodomethane or dimethyl sulfate gave methyl hydrazinecarbodithioate (4). Condensation of 4 with 2-acetylpyridine gave the versatile intermediate, methyl 3-[1-(2-pyridyl)ethylidene]hydrazinecarbodithioate, 5. Reaction of 5 with primary amines gave 4-monosubstituted thiosemicarbazones such as 3 while secondary amines or cyclic amines produced 4,4-disubstituted thiosemicarbazones, 6. In addition, reaction of 5 was not limited to more active nucleophiles, as excellent yields could be obtained with many primary aromatic amines. However, 5 was resistant to reaction with some secondary aromatic amines, such as N-methylaniline.

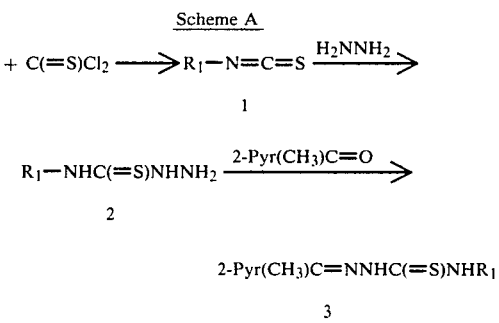

Scheme A

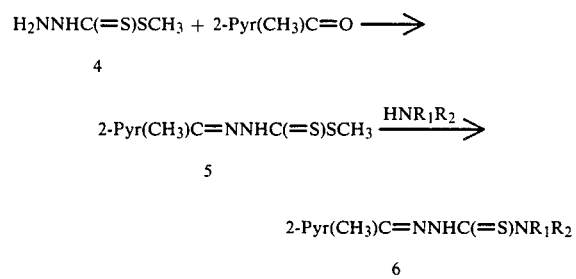

Scheme B

Scheme C involved the reaction of 2-acetylpyridine with hydrazine to yield the hydrazone 7. Reaction of this hydrazone with an isothiocyanate 1 produced a 4-monosubstituted thiosemicarbazone 3. This reaction was especially useful when the required isothiocyanate was commercially available.

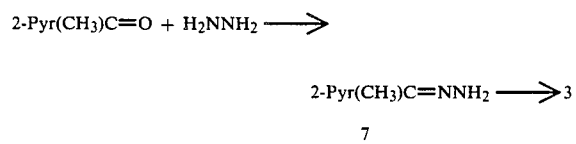

Scheme C

Preparation of Selenosemicarbazones

The synthetic procedures useful for preparing the selenosemicarbazones of this invention are as follows:

Scheme D

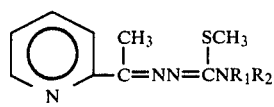

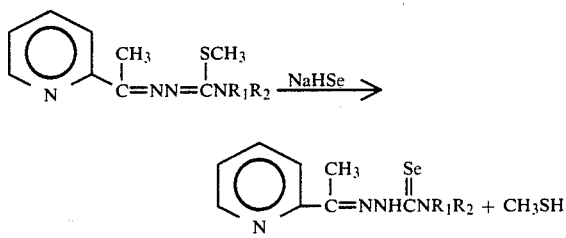

In Scheme D, S-methylation of the thiosemicarbazones was performed in the presence of aqueous or alcoholic base. The resulting products were allowed to react with sodium hydrogen selenide under an inert atmosphere.

Scheme E

Scheme E -continued

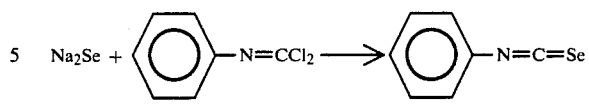

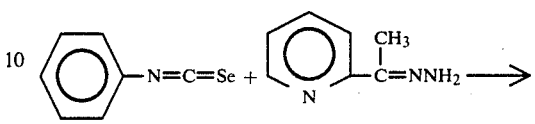

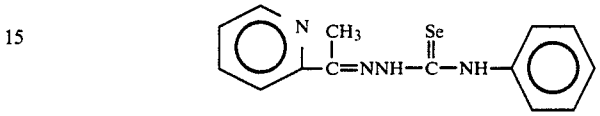

Scheme E represents an alternative method for making the $N^4$-phenyl derivative by a reaction of phenylisoselenocyanate with 2-acetylpyridine hydrazone. The compound obtained, 2-acetylpyridine 4-phenyl-3selenosemicarbazone, was identical to that made by the displacement reaction described in Scheme D. The phenylisoselenocyanate reactant was prepared by a simplified procedure from phenylisocyanide dichloride and sodiumselenide. The latter was generated from elemental selenium and sodium borohydride in ethanol giving sodium hydrogen selenide which was then combined with one equivalent of sodium hydroxide as described by Daniel L. Klayman et al in *J. Amer. Chem. Soc.*, 1973, Vol. 95, page 197.

The following Table 1 further illustrates and provides descriptive information concerning certain 2-acetylpyridine 3-selenosemicarbazones prepared in accordance with Scheme D.

TABLE 1

2-Acetylpyridine 3-Selenosemicarbazones

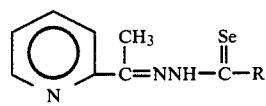

| Compound No. | R | Mp. C.° | Formula | Yield,[a] % | Recryst. solvent |
|---|---|---|---|---|---|
| 1 | —N(piperazinyl)-N-(2-pyridyl) | 182–184 dec | $C_{17}H_{20}N_6Se$ | 49 | $CH_3CN$ |
| 2 | 2,6-dimethylmorpholino | 179–180 dec | $C_{14}N_{20}N_4OSe$ | 34 | $CH_3OH$ |
| 3 | —NH—phenyl | 152–154 dec | $C_{14}N_{14}N_4Se$ | 36 | EtOH |

TABLE 1-continued

2-Acetylpyridine 3-Selenosemicarbazones

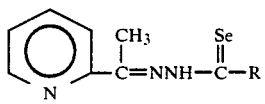

| Compound No. | R | Mp. C.° | Formula | Yield,[a] % | Recryst. solvent |
|---|---|---|---|---|---|
| 4 | ![cyclohexyl-N] | 160–161 | $C_{16}H_{22}N_4Se$ | 49 | $CH_3OH$ |
| 5 | ![piperazinyl-fluorophenyl] | 198–200 dec | $C_{18}H_{20}FN_5Se$ | 36 | $CH_3OH$ |
| 6 | ![azepanyl] | 170–171 dec | $C_{14}H_{20}N_4Se$ | 45 | EtOH |
| 7 | ![azetidinyl] | 175–176 dec | $C_{11}N_{14}N_4Se$ | 38 | EtOH |
| 8 | ![2-methylpiperidinyl] | 135–136 | $C_{14}H_{20}N_4Se$ | 22 | EtOH |
| 9 | ![4-methylpiperidinyl] | 146–147 dec | $C_{14}H_{20}N_4Se$ | 52 | $CH_3OH$ |
| 10 | $-N(CH_3)_2$ | 172–175 dec | $C_{10}H_{14}N_4Se$ | 58 | $CH_3CN$ |
| 11 | $-N(CH_2CH_3)_2$ | 135–136 | $C_{12}N_{18}N_4Se$ | 39 | EtOH |

[a]Yields have not been optimized.

EXAMPLES

The working examples set forth below illustrate, without any implied limitation, the preparation of representative compounds and salts useful in the practice of this invention in the treatment of malaria and leukemia.

EXAMPLE 1

2-Acetylpyridine 4-allyl-3-thiosemicarbazone (Procedure C)

A solution of 2.7 g (0.02 mol) of 2-acetylpyridine hydrazone in 5 ml of MeOH was treated with 3.1 g (0.03 mol) of allyl isothiocyanate and the solution was heated at reflux for 3 hours. The solution was cooled and the product which formed was collected. The crude material was recrystallized 3 times from MeOH, affording 2.5 g (49%) of white needles of 2-acetylpyridine 4-allyl-3-thiosemicarbazone, mp 107° C.

Analysis Calcd. for $C_{11}H_{14}N_4S$: C, 56.38; H, 6.02; N, 23.91; S, 13.68. Found: C, 56.09; H, 6.11; N, 24.36; S, 13.89.

EXAMPLE 2

2-Acetylpyridine 4-cyclohexyl-3-thiosemicarbazone (Procedure C)

A solution of 6.76 g (0.05 mol) of 2-acetylpyridine hydrazone in 10 ml of MeOH was treated with 7.2 g (0.05 mol) of cyclohexyl isothiocyanate and the solution was heated at reflux for 3 hours. The solution was chilled, and the crystals which formed were collected. Recrystallization of the product from 150 ml of MeOH afforded 6.40 g (46%) of white needles of 2-acetylpyridine 4-cyclohexyl-3-thiosemicarbazone, mp 155° C.

Analysis Calcd. for $C_{14}H_{20}N_4S$: C, 60.84; H, 7.29; N, 20.27; S, 11.60. Found: C, 60.76; H, 7.19; N, 20.16; S, 11.73.

EXAMPLE 3

2-Acetylpyridine
4-(2-diethylaminoethyl)-3-thiosemicarbazone
dihydrombromide (Procedure A)

By the application of the procedure of R. S. McElhinney [*J. Chem. Soc.* (c), 950 (1966)], 2-diethylaminoethylisothiocyanate, (bp 54°–55° C./1.5 mm Hg), was prepared in 20% yield.

Analysis Calcd. for $C_7H_{14}N_2S$: C, 53.12; H, 8.92; N, 17.70; S, 20.26. Found: C, 52.97; H, 8.76; N, 18.01; S, 20.47.

A solution of 1 g (0.063 mol) of 2-diethylaminoethylisothiocyanate in 5 ml of MeCN was treated with 0.3 g (0.063 mol) of 85% hydrazine hydrate. The solution was heated at reflux for 10 minutes and the solvent was removed under reduced pressure. The residue was then recrystallized from $C_6H_6$ affording 750 mg (63%) of white needles of 4-(2-diethylaminoethyl)-3-thiosemicarbazide, mp 83°–83.5° C.

Analysis Calcd. for $C_7H_{18}N_4S$: C, 44.18; H, 9.53; N, 29.44; S, 16.85. Found: C, 44.19; H, 9.46; N, 29.56; S, 16.60.

A solution of 605 mg (5 mmol) of 2-acetylpyridine in 10 ml of MeCN was treated with 950 mg (5 mmol) of 4-(2-diethylaminoethyl)-3-thiosemicarbazide and the solution was heated at reflux for 10 hours. The pH of the solution was adjusted to 6 with concentrated HBr and diluted with 15 ml of $Et_2O$. An oil which separated from solution soon solidified. Crystallization of this product for MeOH-MeCN afforded 1.42 g (64%) of yellow crystals of 2-acetylpyridine 4-(2-diethylaminoethyl)-3-thiosemicarbazone dihydrobromide, mp 231° C.

Analysis Calcd. for $C_{14}H_{23}N_5S$ 2HBr: C, 36.93; H, 5.54; N, 15.38; S, 7.04. Found: C, 36.99; H, 5.52; N, 15.30; S, 7.07.

EXAMPLE 4

2-Acetylpyridine
4-(3-fluorophenyl)-3-thiosemicarbazone (Procedure A)

2-Acetylpyridine (2.0 g, 0.0165 mol) in 70 ml of EtOH and 2.78 g (0.015 mol) 4-(3-fluorophenyl)-3-thiosemicarbazide (mp 152°–155° C.) were heated at reflux temperature for 4 hours. The solution was refrigerated overnight and the product was collected. Recrystallization from MeCN afforded 1.1 g (25%) of 2-acetylpyridine 4-(3-fluorophenyl)-3-thiosemicarbazone, mp 159°–160° C.

Analysis Calcd. for $C_{14}H_{13}FN_4S$: C, 58.32; H, 4.54; N, 19.43; S, 11.12. Found: C, 57.87; H, 4.70; N, 19.41; S, 11.08.

EXAMPLE 5

2-Acetylpyridine 4,4-diisobutyl-3-thiosemicarbazone (Procedure B)

A solution of 10 g (0.044 mol) of methyl 3-[1-(2-pyridyl)ethylidene]hydrazinecarbodithioate in 25 ml of MeOH was treated with 7.5 g (0.058 mol) of diisobutylamine and heated at reflux for 6 hours. The solution was chilled and the crystals which formed were collected. Recrystallization from 130 ml of heptane afforded 8.6 g (64%) of yellow needles of 2-acetylpyridine 4,4-diisobutyl-3-thiosemicarbazone, mp 96° C.

Analysis Calcd. for $C_{16}H_{26}N_4S$: C, 62.71; H, 8.55; N, 18.28; S, 10.46. Found: C, 63.27; H, 8.50; N, 18.14; S, 10.21.

EXAMPLE 6

Azacycloheptane-1-thiocarboxylic acid
2-[1-(2-pyridyl)ethylidene]hydrazide (Procedure B)

A solution of 5.0 g (0.022 mol) of methyl 3-[1-(2-pyridyl)ethylidene]hydrazinecarbodithioate in 15 ml of MeOH was treated with 2.2 g (0.022 mol) of hexamethylenimine and heated at reflux for 5 hours. The solution was chilled, scratched and the product which separated was collected. Recrystallization from 150 ml of MeOH afforded 3.4 g (56%) of yellow needles of azacycloheptane-1-thiocarboxylic acid 2-[1-(2-pyridyl)ethylidene]hydrazide, mp 165° C.

Analysis Calcd. for $C_{14}H_{20}N_4S$: C, 60.84; H, 7.29; N, 20.27; S, 11.60. Found: C, 60.91; H, 7.20; N, 20.30; S, 11.89.

EXAMPLE 7

3-Azabicyclo[3.2.2]nonane-3-thiocarboxylic acid
2-[1-(2-pyridyl)ethylidene]hydrazide (Procedure B)

A solution of 3.8 g (0.018 mol) of methyl 3-[1-(2-pyridyl)ethylidene]hydrazinecarbodithioate 2.1 g (0.017 mol) of 3-azabicyclo[3.2.2]nonane was heated at reflux for 5 hours. The solution was cooled, and the product which crystallized was collected. Recrystallization from 160 ml of MeOH afforded 3.34 g (65%) of yellow needles of 3-azabicyclo[3.2.2]nonane-3-thiocarboxylic acid 2-[1-(2-pyridyl)ethylidene]hydrazide, mp 156° C.

Analysis Calcd. for $C_{16}H_{22}N_4S$: C, 63.54; H, 7.33; N, 18.53; S, 10.60. Found: C, 63.51; H, 7.25; N, 18.55; S, 10.67.

EXAMPLE 8

2-Acetylpyridine
4-cyclohexyl-4-methyl-3-thiosemicarbazone (Procedure B)

A solution of 10 g (0.044 mol) of methyl 3-[1-(2-pyridyl)ethylidene]hydrazinecarbodithioate in 24 ml of MeOH was treated with 7.5 g (0.066 mol) of N-methylcyclohexylamine and the solution heated at reflux for 8 hours. The solution was cooled overnight and the product which crystallized was collected. Recrystallization from cyclohexane afforded 9.3 g (72%) of 2-acetylpyridine 4-cyclohexyl-4-methyl-3-thiosemicarbazone, mp 96° C.

Analysis Calcd. for $C_{15}H_{22}N_4S$: C, 62.03; H, 7.64; N, 19.29; S, 11.04. Found: C, 62.07; H, 7.74; N, 19.23; S, 11.14.

EXAMPLE 9

2-Acetylpyridine
4-(2-methylbenzyl)-3-thiosemicarbazone (Procedure B)

Methyl 3-[1-(2-pyridyl)ethylidene]hydrazinecarbodithio ate (4.51 g, 0.02 mol) and 3.64 g (0.03 mol) 2-methylbenzylamine in 25 ml of methanol were heated under reflux for 36 hours followed by overnight refrigeration. The solid material which separated from solution was collected by filtration and recrystallized 3 times from ethanol to afford 3.85 g (48%) of white crystalline 2-acetylpyridine 4-(2-methylbenzyl)-3-thiosemicarbazone having a melting point of 152°–154° C.

Analysis Calcd. for $C_{16}H_{18}N_4S$: C, 64.40; H, 6.08; N, 18.78; S, 10.74. Found C, 64.17; H, 6.23; N, 19.14; S, 10.64.

EXAMPLE 10

4-(2-Pyridyl)-1-piperazinethiocarboxylic acid 2-[1-(2-pyridyl)ethylidene]hydrazide (Procedure B)

Methyl 3-[1-(2-pyridyl)ethylidene]hydrazinecarbodithioate (3.60 g, 0.016 mol) in 40 ml of EtOH was combined with 3.60 g (0.02 mol) of 1-(2-pyridyl)piperazine. The solution was heated at reflux for 18 hours, cooled and the yellow product which separated was collected. Recrystallization from MeCN afforded 3.45 g (60%) of 4-(2-pyrridyl)-1-piperazinethiocarboxylic acid 2-[1-(2-pyridyl)ethylidene]hydrazide, mp 187°–188° C.

Analysis Calcd. for $C_{17}H_{20}N_6S$: C, 59.98; H, 5.92; N, 24.69; S, 9.42. Found: C, 60.65; H, 5.90; N, 24.61; S, 9.41.

EXAMPLE 11

2-Acetylpyridine 4-(2-pyridyl)-3-thiosemicarbazone (Procedure A)

4-(2-Pyridyl)-3-thiosemicarbazide (1.68 g, 0.01 mol) in 125 ml of EtOH and 7.5 ml of glacial acetic acid was treated with 1.21 g (0.01 mol) of 2-acetylpyridine. The solution was heated at reflux for 3 hours, cooled and the product collected. Recrystallization from MeCN afforded 1.8 g (66%) of 2-acetylpyridine 4-(2-pyridyl)-3-thiosemicarbazone, mp 185°–187°0 C.

Analysis Calcd. for $C_{13}H_{13}N_5S$: C, 57.54; H, 4.83; N, 25.81; S, 11.82. Found: C, 57.03; H, 5.08; N, 25.96; S, 12.17.

EXAMPLE 12

2-Acetylpyridine 4-(1-adamantyl)-3-thiosemicarbazone (Procedure A)

A solution of 1.5 g (0.03 mol) of hydrazine hydrate in 50 ml of EtOH was treated with 3.86 g (0.02 mol) of 1-adamantyl isothiocyanate, and stirred for one hour at room temperature. The product was collected and washed two times with EtOH, affording 4.33 g (96%) of 4-(1-adamantyl)-3-thiosemicarbazide, mp 206°–207° C. This thiosemicarbazide is disclosed in Chemical Abstracts, 70:11223 (1969); and in U.S. Pat. No. 3,406,180.

2-Acetylpyridine (2.65 g, 0.022 mol) in 50 ml of EtOH and 2 ml of glacial acetic acid was combined with 4.33 g (0.0195 mol) of 4-(1-adamantyl)-3-thiosemicarbazide, and the solution was heated at reflux for 24 hours. The solution was cooled and the product was collected. Recrystallization from MeCN afforded 3.63 g (50%) of 2-acetylpyridine 4-(1-adamantyl)-3-thiosemicarbazone, mp 172°–173° C.

Analysis Calcd. for $C_{18}H_{24}N_4S$: C, 65.82; H, 7.36; N, 17.06; S, 9.76. Found: C, 66.04; H, 7.22; N, 16.88; S, 9.71.

EXAMPLE 13

2-Acetylpyridine 4,4-dimethyl-3-thiosemicarbazone (Procedure A)

To a solution of 2.39 g (0.02 mol) of 4,4-dimethyl-3-thiosemicarbazide in 75 ml of EtOH was added 2.54 g (0.021 mol) of 2-acetylpyridine. After heating at reflux for eight hours, the solution was cooled and the product was collected. Recrystallization from MeOH afforded 1.2 g (26%) of 2-acetylpyridine 4,4-dimethyl-3-thiosemicarbazone, mp 149°–150° C.

Analysis Calcd. for $C_{10}H_{14}N_4S$: C, 54.03; H, 6.35; N, 25.20; S, 14.42. Found: C, 53.83; H, 6.74; N, 25.25; S, 14.72.

EXAMPLE 14

2-Acetylpyridine 4,4-dimethyl-3-thiosemicarbazone (Procedure B)

Methyl 3-[1-(2-pyridyl)ethylidene]hydrazinecarbodithioate (9.02 g, 0.04 mol) in 30 ml of EtOH was combined with 5.2 g (0.08 mol) of dimethylamine (40% aqueous solution). The resulting solution was heated at reflux for 24 hours and the excess dimethylamine was removed under water-pump aspiration for 15 minutes. The solution was filtered and cooled to give 7.3 g (82%) of bright yellow crystals of 2-acetylpyridine 4,4-dimethyl-3-thiosemicarbazone, mp 155°–156° C. whose infrared spectrum was identical to that of the product made by the method described in Example 13.

EXAMPLE 15

1-Azacycloheptane-1-thiocarboxylic acid 2-[1-(2-pyridyl)propylidene]hydrazide (Procedure B)

Methyl 3-[1-(2-pyridyl)propylidene]hydrazinecarbodithioate (4.77 g, 0.02 mol) and 3.4 ml (3.0 g, 0.03 mol) hexamethylenimine in 25 ml of MeOH were heated under reflux for 48 hours followed by overnight refrigeration. The solid material which separated from solution was collected by filtration and recrystallized from MeOH to afford 3.65 g (63%) of yellow crystalline 1-azacycloheptane-1-thiocarboxylic acid 2-[1-(2-pyridyl)propylidene]hydrazide, mp 117°–119° C.

Analysis Calcd. for $C_{15}N_{22}N_4S$: C, 62.03; H, 7.64; N, 19.29; S, 11.04. Found: C, 62.15; H, 7.64; N, 19.14; S, 11.16.

The compounds listed in Table 1 as 1–11 were prepared by the method exemplified in the following description of the preparation of 2-acetylpyridine 4,4-dimethyl-3-selenosemicarbazone.

EXAMPLE 16

2-Acetylpyridine 4,4-dimethyl-3-selenosemicarbazone (Procedure D)

A suspension of 3.0 g (13.5 mmol) of 2-acetylpyridine 4,4-dimethyl-3-thiosemicarbazone in 10 ml of $H_2O$ was treated with 5 ml of 50% w/w solution of aqueous NaOH. The suspension was stirred for 5 minutes, and then 2.28 g (16.1 mmol) of iodomethane was added dropwise to the rapidly stirred mixture, converting the yellow solid into a yellow oil. The oil was extracted into 50 ml of $Et_2O$ ($3 \times 50$ ml) and brine ($1 \times 50$ ml) and dried ($MgSO_4$). The solvent was removed under reduced pressure and the resulting S-methyl compound of the formula 2-acetylpridine 4,4-dimethyl-3-methylthiosemicarbazone, as an oil, was used without further purification for the succeeding step.

A solution of sodium hydrogen selenide was prepared by combining 1.18 g (15 mmol) of Se with 0.64 g (17 mmol) of sodium borohydride in 25 ml of EtOH under argon. A solution of the S-methyl compound in 25 ml of EtOH was added in a single portion, the reaction mixture was stirred for 40 hours, and poured into 50 ml of 10% aqueous acetic acid. The product was extracted into 50 ml of $CHCl_3$ which was then washed with $H_2O$ ($3 \times 50$ ml), dried over $MgSO_4$, and the solvent was removed under reduced pressure. Crystallization of the selenosemicarbazone from MeCN afforded orange needles. IR: 1615, 1577, 1513, 1494, 1430, 1401, 1382, 1360, 1340, 1296, 1252, 1235, 1157, 977, 778 cm$^{-1}$.

EXAMPLE 17

N-Phenyl-2-[-1-(2-pyridinyl)ethylidene]hydrazinecarboselenoamide (Procedure E)

Absolute ethanol (25 ml) was added with mechanical stirring and ice bath cooling to 3.5 g (45 mmol) of selenium and 1.9 g (50 mmol) of sodium borohydride under an inert atmosphere. The ice bath was removed after initial foaming subsided. The solution was allowed to stir for 20 minutes, was treated with 1.8 g (45 mmol) of NaOH dissolved in 5 ml of water, to which was added 6.53 g (37.5 mmol) of phenylisocyanide dichloride causing the immediate appearance of an opaque orange color. After an additional 4 hours of stirring, the mixture was treated with 120 ml of $H_2O$ and extracted with $3 \times 30$ ml of $Et_2O$. The yellow extracts were combined, dried over $CaCl_2$, and the $Et_2O$ was removed under reduced pressure. The opaque product was redissolved in 20 ml of petroleum ether, filtered, and the solvent was removed yielding 3.6 g (52%) of phenylisoselenocyanate as a pungent red oil which was used without further purification. IR: 2110 (N=C=Se), 2050, 1590, 1480, 850, 755 cm$^{-1}$.

To a solution of 2.6 g (20 mmol) of 2-acetylpyridine hydrazone in 25 ml of $CH_3CN$ was added 3.6 g (20 mmol) of phenylisoselenocyanate. The clear red solution was heated with stirring to 45° C. for 3 hours, the solution was cooled to room temperature, and the crystals which separated were collected. Recrystallization of the product from EtOH gave 2.83 g (45%) of N-phenyl-2-[1-(2-pyridinyl)ethylidene]hydrazinecarboselenoamide as fine yellow needles, mp 153°–156° C.

TEST METHODS

Biological Methods. The 2-acetylpyridine thiosemicarbazones and their selenosemicarbazone analogs were tested for antimalaria activity at the Dr. Leo Rane Laboratory, University of Miami, Fla., against a drug-sensitive strain of *Plasmodium berghei* (strain KBG 173) in mice. Five mice per dose level are infected by the intraperitoneal administration of parasitized erythrocytes. Untreated infected animals, which serve as controls, die, on the average, after 6.2 days. A candidate drug is given 72 hours after the mice are infected and is judged to be "toxic" if they die before the 6th day, "inactive" if they die between the 6th and 12th day, "active" if the mean survival time is at least doubled, and "curative" if the mice survive at least 60 days post infection. Compounds which are "active" or "curative" at a dose of 40 mg/kg are retested at several lower dose levels, but results are not reported unless extension of mouse survival time is observed. Details of the test procedure were reported by Osdene, Russel, and Rane in *J. Med. Chem.*, 1967, Vol. 10, page 431.

UTILITY

Antimalarial activity. The ability to cure mice infected with *Plasmodium berghei* was investigated in a series of $N^4,N^4$-disubstituted selenosemicarbazones of 2-acetylpyridine (Table 2). The most potent in the selenium series produced cures at the dosage level of 20 mg/kg.

Surprisingly, the selenosemicarbazones appear to be less toxic than their corresponding sulfur analogs.

TABLE 2

Comparison of Antimalarial Activity of Related 2-Acetylpyridine Selenosemicarbazones and Thiosemicarbazones Against *Plasmodium berghei* in Mice

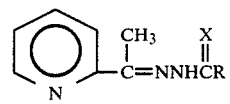

| Compound | Increase in the Mean Survival Time (days) and Number of Cures at given Dosage, mg/kg[b] | | | | | | | | | | | |
|---|---|---|---|---|---|---|---|---|---|---|---|---|
| | X=Se | | | | | | X=S | | | | | |
| No.[a] | 20 | 40 | 80 | 160 | 320 | 640 | 20 | 40 | 80 | 160 | 320 | 640 |
| 1 | — | 0.3 | 4.8 | C (2/5) | C (3/5) | C (5/5) | C (3/5) | C (4/5) | C (5/5) | C (2/5) | 0.7 T (2/5) | T (5/5) |
| 2 | C (2/5) | C (5/5) | C (1/5) T (3/5) | T (5/5) | T (5/5) | T (5/5) | C (3/5) | C (2/5) T (2/5) | — | T (5/5) | — | T (5/5) |
| 3 | — | 1.5 | — | 5.2 T (3/5) | — | T (5/5) | — | 3.1 | 4.7 | 11.1 A | C (1/5) T (1/5) | C (2/5) T (2/5) |
| 4 | −0.1 | 0.8 | 5.9 | C (1.5) | C (2/5) | C (3/5) | C (1/5) | C (3/5) | C (3/5) | C (5/5) | 0.2 | 0.4 T (4/5) |
| 5 | 0.4 | 0.4 | 0.4 | 0.6 | 2.0 | C (1/5) | — | C (1/5) | — | C(5/5) T (1/5) | — T (2/5) | 9.0 A T (3/5) |
| 6 | — | 1.7 | 4.6 | 7.3 | C (2/5) | C (2/5) | — | 6.2 A | C (4/5) | C (3/5) | C (2/5) | C (2/5) |
| 7 | 3.8 | 6.5 | C (1/5) T (2/5) | C (1/5) T (4/5) | T (5/5) | T (5/5) | — | 1.7 | — | T (5/5) | — | T (5/5) |
| 8 | 0.2 | 2.7 | 5.4 | C (3/5) | C (2/5) T (2/5) | 9.9 A T (3/5) | — | C (3/5) | — | T (5/5) | — | T (5/5) |
| 9 | — | 8.6 A | — | C (4/5) | — | T (5/5) | — | C (3/5) | — | T (5/5) | — | T (5/5) |
| 10 | C (1/5) | C (1/5) T (1/5) | T (5/5) | C (1/5) T (4/5) | T (5/5) | T (5/5) | — | 0.5 T (3/5) | — | T (5/5) | — | T (5/5) |
| 11 | 0.8 | 4.3 | 5.3 | C (3/5) T (2/5) | T (5/5) T (4/5) | — | — | 7.2 A | C (1/5) T (1/5) | C (1/5) T (2/5) | — | T (5/5) |

[a]R group are identical for seleno- and thiosemicarbazones on the same line as defined in Table 1.
[b]T = toxic, A = active, C = cure.

Antitumor activity. The evaluation of selenosemicarbazones for antitumor activity against the P338 leukemia cell line in mice were found to be active. Compounds are considered active when their text/control (T/C) value exceeds 125. The compound depicted by the formula:

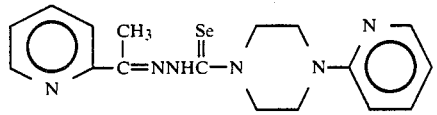

has T/C values of 133 and 126 at varying dose levels. Additionally, the compound depicted by the formula:

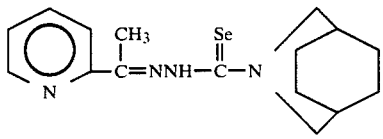

has T/C values of 125, 129 and 133 at varying dose levels.

We claim:

1. A compound of the formula

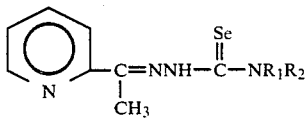

or a pharmaceutically-acceptable acid addition salt wherein and $R_1$ and $R_2$ are taken together with the nitrogen atom to which they are attached to form a heterocyclic ring selected from the group consisting of:
(1) piperazinyl; or piperazinyl substituted with, phenyl, trifluoromethylphenyl, halophenyl, benzyl, or pyridyl;
(2)

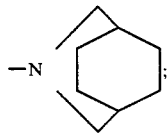

(3) alkylenimino which is mono- or disubstituted with lower alkyl, hydroxy, phenyl or benzyl wherein the alkylene moiety contains 5 or 6 carbon atoms; and
(4) morpholino; or di-lower alkylmorpholino.

2. A compound of the formula

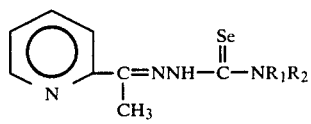

or a pharmaceutically-acceptable acid addition salt wherein $NR_1R_2$ is selected from the group consisting essentially of:

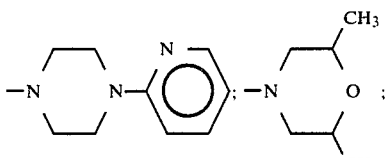

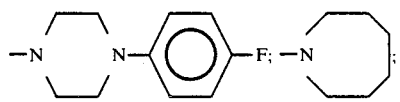

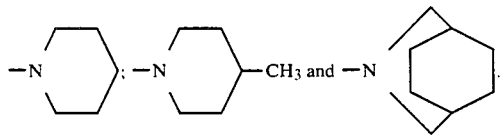

3. A compound or salt of claim 2 wherein the compound has the name 1,4-diaza-4-(2-pyridyl)cyclohexane-1-selenocarboxylic acid 2[1-(2-pyridyl)ethylidene]hydrazide.

4. A compound or salt of claim 2 wherein the compound has the name 3,5-dimethylmorpholine-1-selenocarboxylic acid 2-[1-(2-pyridyl)ethylidene]hydrazide.

5. A compound or salt of claim 2 wherein the compound has the name 1,4-diaza-4-(4-fluorophenyl)cyclohexane-1-selenocarboxylic acid 2-[1-(2-pyridyl)ethylidene]hydrazide.

6. A compound or salt of claim 2 wherein the compound has the name 1-azacycloheptane-1-selenocarboxylic acid 2-[1-(2-pyridyl)ethylidene]hydrazide.

7. A compound or salt of claim 2 wherein the compound has the name 2-methylpiperidine-1-selenocarboxylic acid 2-[1-(2-pyridyl)ethylidene]hydrazide.

8. A compound or salt of claim 2 wherein the compound has the name 4-methylpiperidine-1-selenocarboxylic acid 2-[1-(2-pyridyl)ethylidene]hydrazide.

9. A compound or salt of claim 2 wherein the compound has the name 3-azabicyclo[3.2.2]nonane-3-selenocarboxylic acid 2-[1-(2-pyridyl)ethylidene]hydrazide.

* * * * *